US011780805B2

(12) United States Patent
Hurley et al.

(10) Patent No.: US 11,780,805 B2
(45) Date of Patent: *Oct. 10, 2023

(54) CARBAMOYL PHENYLALANINOL COMPOUNDS AND USES THEREOF

(71) Applicant: AXSOME MALTA LTD., Qormi (MT)

(72) Inventors: Fionn Hurley, Baldoyle (IE); Lawrence Patrick Carter, Palo Alto, CA (US)

(73) Assignee: Axsome Malta Ltd., Qormi (MT)

( * ) Notice: Subject to any disclaimer, the term of this patent is extended or adjusted under 35 U.S.C. 154(b) by 0 days.

This patent is subject to a terminal disclaimer.

(21) Appl. No.: 17/470,063

(22) Filed: Sep. 9, 2021

(65) Prior Publication Data

US 2022/0098145 A1 Mar. 31, 2022

Related U.S. Application Data

(63) Continuation of application No. 16/891,464, filed on Jun. 3, 2020, now Pat. No. 11,149,000, which is a continuation of application No. 16/338,925, filed as application No. PCT/US2017/055598 on Oct. 6, 2017, now Pat. No. 10,710,958.

(60) Provisional application No. 62/404,917, filed on Oct. 6, 2016.

(51) Int. Cl.
*C07C 271/66* (2006.01)

(52) U.S. Cl.
CPC ........ *C07C 271/66* (2013.01); *C07C 2601/16* (2017.05)

(58) Field of Classification Search
CPC .................................................. C07C 271/66
See application file for complete search history.

(56) References Cited

U.S. PATENT DOCUMENTS

| | | | |
|---|---|---|---|
| 8,232,315 | B2 | 7/2012 | Lee et al. |
| 8,623,913 | B2 | 1/2014 | Melnick et al. |
| 9,403,761 | B2 | 8/2016 | Kang et al. |
| 9,833,432 | B2 | 12/2017 | Kang et al. |
| 10,314,808 | B2 | 6/2019 | Kang et al. |
| 10,888,542 | B2 | 1/2021 | Kang et al. |
| 2019/0247356 | A1 | 8/2019 | Kang et al. |

FOREIGN PATENT DOCUMENTS

| | | | |
|---|---|---|---|
| WO | 2006050037 | A1 | 5/2006 |
| WO | 2006133393 | A1 | 12/2006 |
| WO | 2007001841 | A1 | 1/2007 |
| WO | 2010150995 | A2 | 12/2010 |
| WO | 2011005473 | A2 | 1/2011 |
| WO | 2011055944 | A2 | 5/2011 |
| WO | 2012002687 | A2 | 1/2012 |
| WO | 2012002688 | A2 | 1/2012 |
| WO | 2014164969 | A1 | 10/2014 |
| WO | 2015010014 | A1 | 1/2015 |
| WO | 2015130121 | A1 | 9/2015 |

OTHER PUBLICATIONS

Schmeichel, et al. Neuropharmacology 64 (2013) 321-328.*
Ozen, et al. Turk Psikiyatri Dergisi 2007; 18 (3), 1-8.*
Flores-Martinez, et al. International Journal of Peptides, vol. 2017, Article ID 7386809, 1-9.*
Semkovska, et al. . (abstract), Encephale. Sep.-Oct. 2001; 27(5):405-15.*
Callicott, et al. Cerebral Cortex, Nov. 2000; 10: 1078-1092.*
Grisby, et al. (abstract), Archives of Physical Medicine and Rehabilitation vol. 74, Issue 12, Dec. 1993, 1350-1353.*
"Examination Report corresponding to European Application No. 17790906.6 dated Aug. 17, 2020".
"International Preliminary Report on Patentability corresponding to International Application No. PCT/US2017/055598 dated Apr. 18, 2019".
"International Search Report and Written Opinion corresponding to International Application No. PCT/US2017/055598 dated Jan. 3, 2018".
"Office Action corresponding to Japanese Application No. 2019-518480 dated Aug. 16, 2021".
"Office Action corresponding to Chinese Application No. 201780075629.4 dated Jan. 21, 2021".
"Office Action corresponding to Indonesian Application No. PID201903611 dated Feb. 15, 2021".
"Phenprobamate, Wikipedia, https://en.wikipedia.org/wiki/Phenprobamate, last edited Apr. 2, 2016, accessed Sep. 24, 2019".
"Written Opinion corresponding to Singapore Application No. 11201903076Q dated Jun. 7, 2020".
Baladi, Michelle G, et al., "Characterization of the Neurochemical and Behavioral Effects of Solriamfetol (JZP-110), a Selective Dopamine and Norepinephrine Reuptake Inhibitor", J. Pharmacol. Exp. Ther. 366:367-376 (Aug. 2018).
Billes, Sonja K, et al., "Inhibition of Dopamine and Norepinephrine Reuptake Produces Additive Effects on Energy Balance in Lean and Obese Mice", Neuropsychopharmacology 32:822-834 (2007).
Bron, Morgan , et al., "Indirect Treatment Comparison of the Efficacy of Solriamfetol (JZP-110), Modafinil, and Armodafinil for the Treatment of Excessive Sleepiness in Obstructive Sleep Apnea", Ann. Mtg. Acad. Managed Care Pharmacy Nexus, Oct. 22-25, 2018, Orlando, Florida.
Drury , et al., ""The Role of the Dopamine Transporter (DAT) in the Development of PTSD in Preschool Children", Journal of Traumatic Stress 22(6):534-539 (2009)".
Johnston, Janice L, "A Role for Norepinephrine Metabolism in Energy Balance and Obesity: A Review", Can. Inst. Food Sci. Techonol. J. 20(5):331-335 (1987).
Mignot, Emmanuel , et al., "Canine cataplexy is preferentially controllable by adrenergic mechanisms: evidence using monoamine selective uptake inhibitors and release enhancers", Psychopharmacology 113:76-82 (1993).

(Continued)

*Primary Examiner* — Shawquia Jackson
(74) *Attorney, Agent, or Firm* — Myers Bigel, P.A.

(57) ABSTRACT

The present invention relates to carbamoyl phenylalaninol compounds and methods of using the same to treat disorders.

18 Claims, No Drawings

(56) References Cited

OTHER PUBLICATIONS

Mitchell, Heather A, et al., "Good Night and Good Luck: Norepinephrine in Sleep", Biochem Pharmacol. 79(6):801-809 (Mar. 15, 2010).

Segman, et al., ""Association between the dopamine transporter gene and posttraumatic stress disorder", Molecular Psychiatry 7(8):903-907 (2002)".

Zhou, Jia, "Norepinephrine transporter inhibitors and their therapeutic potential", Drugs Future. 29(12):1235-1244 (Dec. 2004).

"Dopamine in the brain, edited by Guozhang Jin, Shanghai Science and Technology Publishing House, Nov. 2010, the first printing of the first edition, pp. 673-677".

"Neuropsychiatry, edited by Chunmei Han, military Medical Science Press, Aug. 2006, the first printing of the first edition, pp. 32-33".

"Office Action corresponding to Chinese Application No. 201780075629.4 dated Oct. 20, 2021".

"Office Action corresponding to European Application No. 17790906.6 dated Dec. 6, 2021".

"Office Action corresponding to Vietnamese Application No. 1-2019-02165 dated Jun. 13, 2022".

"Office Action corresponding to Philippine Application No. 1-2019-500751 dated Jan. 25, 2022".

"Office Action corresponding to Chinese Application No. 201780075629.4 dated Apr. 26, 2022".

"Office Action corresponding to Philippine Application No. 1-2019-500751 dated May 12, 2022".

"Office Action corresponding to Indonesian Application No. PID201903611 dated Aug. 2, 2022".

"Office Action corresponding to Indonesian Application No. PID201903611 dated Feb. 16, 2023".

"Office Action corresponding to Malaysian Application No. PI2019001915 dated Jan. 31, 2023".

"Examination Report corresponding to Singapore Application No. 11201903076Q dated Jan. 31, 2023".

"Office Action corresponding to Korean Application No. 10-2019-7013113 dated Nov. 16, 2022".

"Office Action corresponding to Korean Application No. 10-2019-7013113 dated May 26, 2023".

"Office Action corresponding to Philippine Application No. 1/2019/500751 dated Mar. 23, 2023".

"Office Action corresponding to Thai Application No. 1901002142 dated Mar. 21, 2023".

* cited by examiner

CARBAMOYL PHENYLALANINOL COMPOUNDS AND USES THEREOF

STATEMENT OF PRIORITY

This application is a continuation of and claims priority to U.S. patent application Ser. No. 16/891,464, filed Jun. 3, 2020, now allowed, which is a continuation of and claims priority to U.S. patent application Ser. No. 16/338,925, filed Apr. 2, 2019, now U.S. Pat. No. 10,710,958, which is a 35 U.S.C. § 371 national phase application of PCT Application PCT/US2017/055598 filed Oct. 6, 2017, which claims the benefit, under 35 U.S.C. § 119(e), of U.S. Provisional Application No. 62/404,917, filed Oct. 6, 2016, the entire contents of each of which are incorporated by reference herein in its entirety.

FIELD OF THE INVENTION

The present invention relates to carbamoyl phenylalaninol compounds and methods of using the same to treat disorders.

BACKGROUND OF THE INVENTION (R)-2-amino-3-phenylpropyl carbamate (APC) is a phenylalanine analog that has been demonstrated to be useful in the treatment of a variety of disorders, including excessive daytime sleepiness, cataplexy, narcolepsy, fatigue, depression, bipolar disorder, fibromyalgia, and others. See, for example, U.S. Pat. Nos. 8,232,315; 8,440,715; 8,552,060; 8,623,913; 8,729,120; 8,741,950; 8,895,609; 8,927,602; 9,226,910; and 9,359,290; and U.S. Publication Nos. 2012/0004300 and 2015/0018414. Methods for producing APC (which also has other names) and related compounds can be found in U.S. Pat. Nos. 5,955,499; 5,705,640; 6,140,532 and 5,756,817. All of the above patents and applications are hereby incorporated by reference in their entireties for all purposes.

The present invention overcomes shortcomings in the art by providing analogs of APC and a method of using the same to treat disorders.

SUMMARY OF THE INVENTION

The present invention relates to the identification of analogs of APC. Accordingly, the present invention relates to a compound of Formula I:

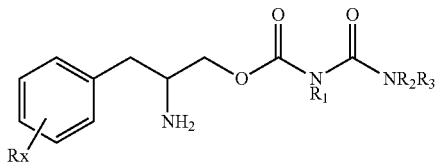

wherein
R is optionally substituted lower alkyl of 1 to 8 carbon atoms, halogen, optionally substituted alkoxy containing 1 to 3 carbon atoms, nitro, hydroxy, cyano, trifluoromethyl, or optionally substituted thioalkoxy containing 1 to 3 carbon atoms;
x is an integer of 0 to 3, with the proviso that R may be the same or different when x is 2 or 3;
$R_1$, $R_2$, and $R_3$ are independently hydrogen, optionally substituted lower alkyl of 1 to 8 carbon atoms, optionally substituted aryl, optionally substituted arylalkyl, or optionally substituted cycloalkyl of 3 to 7 carbon atoms; or
$R_2$ and $R_3$ can be joined to form a 5 to 7-membered heterocycle optionally substituted with a member selected from the group consisting of alkyl and aryl groups, wherein the heterocycle can comprise 1 to 2 nitrogen atoms and 0 to 1 oxygen atom, wherein the nitrogen atoms are not directly connected with each other or with the oxygen atom;
or a pharmaceutically acceptable salt thereof.

The invention further relates to compositions and pharmaceutical compositions comprising the compound of the invention.

The invention additionally relates to a method of treating a disorder amenable to treatment with APC, e.g., narcolepsy, cataplexy, excessive daytime sleepiness, drug addiction, sexual dysfunction, fatigue, fibromyalgia, attention deficit/hyperactivity disorder, restless legs syndrome, depression, bipolar disorder, or obesity, in a subject in need thereof, or promoting smoking cessation in a subject in need thereof, comprising administering to the subject the compound of the invention.

The present invention is explained in greater detail in the drawings herein and the specification set forth below.

DETAILED DESCRIPTION OF THE INVENTION

The present invention can be embodied in different forms and should not be construed as limited to the embodiments set forth herein. Rather, these embodiments are provided so that this disclosure will be thorough and complete, and will fully convey the scope of the invention to those skilled in the art. For example, features illustrated with respect to one embodiment can be incorporated into other embodiments, and features illustrated with respect to a particular embodiment can be deleted from that embodiment. In addition, numerous variations and additions to the embodiments suggested herein will be apparent to those skilled in the art in light of the instant disclosure, which do not depart from the instant invention.

Unless otherwise defined, all technical and scientific terms used herein have the same meaning as commonly understood by one of ordinary skill in the art to which this invention helones. The terminology used in the description of the invention herein is for the purpose of describing particular embodiments only and is not intended to be limiting of the invention.

Unless the context indicates otherwise, it is specifically intended that the various features of the invention described herein can be used in any combination.

Moreover, the present invention also contemplates that in some embodiments of the invention, any feature or combination of features set forth herein can be excluded or omitted.

To illustrate, if the specification states that a complex comprises components A, B and C, it is specifically intended that any of A, B or C, or a combination thereof, can be omitted and disclaimed singularly or in any combination.

All publications, patent applications, patents, and other references mentioned herein are incorporated by reference herein in their entirety for all purposes.

As used herein, "a," "an," or "the" can mean one or more than one. For example, "a," cell can mean a single cell or a multiplicity of cells.

Also as used herein, "and/or" refers to and encompasses any and all possible combinations of one or more of the associated listed items, as well as the lack of combinations when interpreted in the alternative ("or").

Furthermore, the term "about," as used herein when referring to a measurable value such as an amount of a compound or agent of this invention, dose, time, temperature, and the like, is meant to encompass variations of ±10%, ±5%, ±1%, ±0.5%, or even ±0.1% of the specified amount.

The term "consists essentially of" (and grammatical variants), as applied to the compositions of this invention, means the composition can contain additional components as long as the additional components do not materially alter the composition. The term "materially altered," as applied to a composition, refers to an increase or decrease in the therapeutic effectiveness of the composition of at least about 20% or more as compared to the effectiveness of a composition consisting of the recited components.

The term "therapeutically effective amount" or "effective amount," as used herein, refers to that amount of a composition, compound, or agent of this invention that imparts a modulating effect, which, for example, can be a beneficial effect, to a subject afflicted with a disorder, disease or illness, including improvement in the condition of the subject (e.g., in one or more symptoms), delay or reduction in the progression of the condition, prevention or delay of the onset of the disorder, and/or change in clinical parameters, disease or illness, etc., as would be well known in the art. For example, a therapeutically effective amount or effective amount can refer to the amount of a composition, compound, or agent that improves a condition in a subject by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%.

"Treat" or "treating" or "treatment" refers to any type of action that imparts a modulating effect, which, for example, can be a beneficial effect, to a subject afflicted with a disorder, disease or illness, including improvement in the condition of the subject (e.g., in one or more symptoms), delay or reduction in the progression of the condition, and/or change in clinical parameters, disease or illness, etc., as would be well known in the art.

A "disorder amenable to treatment with APC" refers to any disorder in which administration of APC to a subject results in the treatment of one or more symptoms of the disorder in the subject.

"Pharmaceutically acceptable," as used herein, means a material that is not biologically or otherwise undesirable, i.e., the material can be administered to an individual along with the compositions of this invention, without causing substantial deleterious biological effects or interacting in a deleterious manner with any of the other components of the composition in which it is contained. The material would naturally be selected to minimize any degradation of the active ingredient and to minimize any adverse side effects in the subject, as would be well known to one of skill in the art (see, e.g., *Remington's Pharmaceutical Science*, 21$^{st}$ ed. 2005).

"Concurrently" means sufficiently close in time to produce a combined effect (that is, concurrently can be simultaneously, or it can be two or more events occurring within a short time period before or after each other). In some embodiments, the administration of two or more compounds "concurrently" means that the two compounds are administered closely enough in time that the presence of one alters the biological effects of the other. The two compounds can be administered in the same or different formulations or sequentially. Concurrent administration can be carried out by mixing the compounds prior to administration, or by administering the compounds in two different formulations, for example, at the same point in time but at different anatomic sites or using different routes of administration.

The term "alkyl" denotes a straight or branched hydrocarbon chain containing 1-12 carbon atoms, e.g., 1-8, 1-6, or 1-4 carbon atoms. Examples of alkyl groups include methyl, propyl, isopropyl, butyl, isobutyl, tert-butyl, and the like.

By "substituted alkyl" is meant an alkyl in which an atom of the alkyl is substituted with, for example, a carbon, nitrogen, sulfur, oxygen, silicon, or halogen atom, or alternatively a nitrogen, sulfur, oxygen, or halogen atom. The term encompasses substituents on alkyl, alkenyl, alkynyl, and cycloalkyl groups.

Examples of substituents that can be attached to any atom of the alkyl group in a "substituted alkyl" include cyclyl groups, heterocyclyl groups; aryl groups, heteroaryl groups, amino groups, amido groups, nitro groups, cyano groups, azide groups, hydroxy groups, alkoxy groups, acyloxy groups, thioalkoxy groups, acyl thioalkoxy groups, halogen groups, sulfonate groups, sulfonamide groups, ester groups, carboxylic acids, oxygen (e.g., a carbonyl group), and sulfur (e.g., a thiocarbonyl group). Substituents also include any chemical functional group that imparts improved water-solubility to the molecule (e.g., carboxylic acid, carboxylic ester, carboxamide, morpholino, piperazinyl, imidazolyl, thiomorpholino, or tetrazolyl groups; both unsubstituted and substituted).

The terms "halo" and "halogen" refer to any radical of fluorine, chlorine, bromine or iodine.

The terms "alkoxy" denotes an oxygen linked to an alkyl or substituted alkyl as defined above.

The term "thioalkoxy" denotes a sulfur linked to an alkyl or substituted alkyl as defined above.

The term "cycloalkyl" denotes a monocyclic saturated carbocyclic group containing 3-8 carbon atoms, e.g., 3-6 carbon atoms. Examples of cycloalkyl groups include cyclopropyl, cyclobutyl, cyclopentyl, cyclohexyl, cycloheptyl, cyclooctyl, and the like.

The term "aryl" refers to an aromatic 5-8 membered monocyclic or 8-12 membered bicyclic ring system wherein 0, 1, 2, or 3 atoms of each ring can be substituted by a substituent. The term also includes aromatic bicyclic ring systems in which a hydrogen atom has been added to one, two, or three of the ring carbons in one of the rings (e.g., a partially saturated ring). Examples of aryl groups include phenyl, naphthyl and the like.

The teen "arylalkyl" denotes an aryl group linked to an alkyl or substituted alkyl as defined above.

The term "heterocycle" refers to an aromatic or nonaromatic 5-8 membered monocyclic or 8-12 membered bicyclic ring system comprising 1-3 heteroatoms if monocyclic or 1-6 heteroatoms if bicyclic, said heteroatoms selected from O, N, or S, wherein 0, 1, 2 or 3 atoms of each ring can be substituted by a substituent. The term also includes aromatic and nonaromatic bicyclic ring systems in which a hydrogen atom has been added to one, two, or three of the ring carbons in one of the rings (e.g., a partially saturated ring). Examples of heterocycle groups include pyridyl, furyl or furanyl, benzofuranyl, imidazolyl, benzimidazolyl, pyrimidinyl, thiophenyl or thienyl benzothiophenyl, quinolinol, isoquinolinyl, dihydroquinolinyl, dihydroisoquinolinyl, naphthyridinyl, dihydronaphthyridinyl, quinazolinyl, indolyl, indazolyl, thiazolyl, benzothiazolyl, oxazinyl, benzooxazinyl, oxazolyl, benzooxazolyl, dihydrobenzodioxinyl, and the like.

Suitable substituents for aryl and heteroaryl groups are the same as the substituents for alkyl groups.

The present invention relates to the identification and characterization of analogs of APC that are expected to have equivalent or similar biological and therapeutic activity. The structure of APC free base is given below.

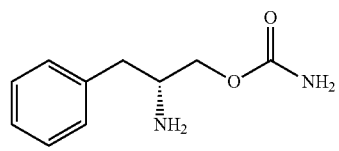 [SMILES: NC(=O)OC[C@H](N)Cc1ccccc1]

Thus, one aspect of the invention relates to a compound of Formula I:

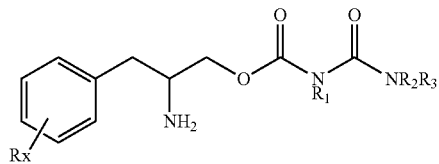

wherein
R is optionally substituted lower alkyl of 1 to 8 carbon atoms, halogen, optionally substituted alkoxy containing 1 to 3 carbon atoms, nitro, hydroxy, cyano, trifluoromethyl, or optionally substituted thioalkoxy containing 1 to 3 carbon atoms;
x is an integer of 0 to 3, with the proviso that R may be the same or different when x is 2 or 3;
$R_1$, $R_2$, and $R_3$ are independently hydrogen, optionally substituted lower alkyl of 1 to 8 carbon atoms, optionally substituted aryl, optionally substituted arylalkyl, or optionally substituted cycloalkyl of 3 to 7 carbon atoms; or
$R_2$ and $R_3$ can be joined to form a 5 to 7-membered heterocycle optionally substituted with a member selected from the group consisting of alkyl and aryl groups, wherein the heterocycle can comprise 1 to 2 nitrogen atoms and 0 to 1 oxygen atom, wherein the nitrogen atoms are not directly connected with each other or with the oxygen atom;
or a pharmaceutically acceptable salt thereof.

In some embodiments, the compound is a compound of Formula II:

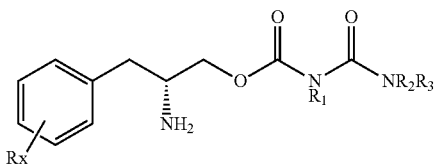

or a pharmaceutically acceptable salt thereof.

In some embodiments, the compound is compound 1 (phenylalaninol allophanate):

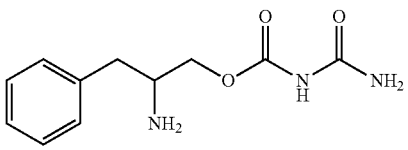 [SMILES: NC(=O)NC(=O)OCC(N)Cc1ccccc1]

or a pharmaceutically acceptable salt thereof.

In some embodiments, the compound is compound 2 (D-phenylalaninol allophanate):

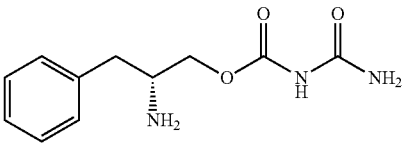 [SMILES: NC(=O)NC(=O)OCC(N)Cc1ccccc1]

or a pharmaceutically acceptable salt thereof.

In some embodiments, the compound of Formula I is not compound 1 or 2.

The compounds, formulations and unit dosage forms provided herein can be utilized to achieve immediate release of the compound of the invention, as well as pharmaceutically acceptable salts, hydrates, isomers, including tautomers, solvates and complexes of the compound.

Suitable salts of the compound of the invention include, without limitation, acetate, adipate, alginate, aspartate, benzoate, butyrate, citrate, fumarate, glycolate, hemisulfate, heptanoate, hexanoate, hydrochloride, hydrobromide, hydroiodide, 2-hydroxyethanesulfonate, lactate, maleate, malonate, methanesulfonate, nicotinate, nitrate, oxalate, palmoate, pectinate, persulfate, hydroxynapthoate, pivalate, propionate, salicylate, succinate, sulfate, tartrate, thiocyanate, tosylate and undecanoate. Other acids, such as oxalic, while not in themselves pharmaceutically acceptable, can be employed in the preparation of salts useful as intermediates in obtaining the compound of the invention and their pharmaceutically acceptable acid addition salts. In certain embodiments, the salt is the hydrochloride salt.

Compounds of the formulae herein include those having quaternization of any basic nitrogen-containing group therein.

The discussion herein is, for simplicity, provided without reference to stereoisomerism. Those skilled in the art will appreciate that the compound of the invention can contain one or more asymmetric centers and thus occur as racemates and racemic mixtures and single optical isomers. All such isomeric forms of these compounds are expressly included in the present invention.

Unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$- or $^{14}C$-enriched carbon are within the scope of this invention. Such compounds are useful, for example, as analytical tools or probes in biological assays.

The discussion herein is also provided without reference to polymorphs, hydrates, clathrates, solvates, inclusion compounds, isomers, or other forms of the compound. All such forms of these compounds are expressly included in the present invention.

Further, the compounds of the invention include prodrugs of the compounds that are converted to the active compound in vivo. For example, the compound can be modified to enhance cellular permeability (e.g., by esterification of polar groups) and then converted by cellular enzymes to produce the active agent. Methods of masking charged or reactive moieties as a pro-drug are known by those skilled in the art (see, e.g., P. Korgsgaard-Larsen and H. Bundgaard, A Textbook of Drug Design and Development, Reading U.K., Harwood Academic Publishers, 1991).

The term "prodrug" refers to compounds that are rapidly transformed in vivo to yield the parent compound of the above formula, for example, by hydrolysis in blood, see, e.g., T. Higuchi and V. Stella, Prodrugs as Novel delivery Systems, Vol. 14 of the A.C.S. Symposium Series and in Edward B. Roche, ed., Bioreversible Carriers in Drug Design, American Pharmaceutical Association and Pergamon Press, 1987, both of which are incorporated by reference herein. See also U.S. Pat. No. 6,680,299. Exemplary prodrugs include a prodrug that is metabolized in vivo by a subject to an active drug having an activity of the compounds as described herein, wherein the prodrug is an ester of an alcohol or carboxylic acid group, if such a group is present in the compound; an amide of an amine group or carboxylic acid group, if such groups are present in the compound; a urethane of an amine group, if such a group is present in the compound; an acetal or ketal of an alcohol group, if such a group is present in the compound; a N-Mannich base or an imine of an amine group, if such a group is present in the compound; or a Schiff base, oxime, acetal, enol ester, oxazolidine, or thiazolidine of a carbonyl group, if such a group is present in the compound, such as described, for example, in U.S. Pat. Nos. 6,680,324 and 6,680,322.

The term "pharmaceutically acceptable prodrug" (and like terms) as used herein refers to those prodrugs of the compound of the present invention which are, within the scope of sound medical judgment, suitable for use in contact with the tissues of humans and/or other animals without undue toxicity, irritation, allergic response and the like, commensurate with a reasonable risk/benefit ratio, and effective for their intended use, as well as the zwitterionic forms, where possible, of the compound of the invention.

The compound of the invention may be synthesized by methods known in the art. In some embodiments, compounds such as compound 1 and compound 2 may be synthesized from phenylalaninol or APC using excess cyanate, e.g. sodium cyanate in an acidic reaction medium.

Another aspect of the invention relates to a composition, e.g., a dosage form, comprising the compound of the invention. In some embodiments, the composition is a pharmaceutical composition comprising the compound of the invention and a pharmaceutically acceptable carrier, In some embodiments, the dosage form is an oral dosage form, e.g., a tablet or a capsule, e.g., an immediate release dosage form.

In some embodiments, the dosage form is an immediate release tablet that releases at least 85%, e.g., at least 85%, 90%, 95%, 96%, 97%, 98%, or 99%, of the compound of the invention contained therein within a period of less than 15 minutes after administration of the tablet to a subject.

Formulations of the compound of the invention, including immediate release formulations, may be processed into unit dosage forms suitable for oral administration, such as for example, filled capsules, compressed tablets or caplets, or other dosage form suitable for oral administration using conventional techniques. Immediate release dosage forms prepared as described may be adapted for oral administration, so as to attain and maintain a therapeutic level of the compound over a preselected interval. In certain embodiments, an immediate release dosage form as described herein may comprise a solid oral dosage form of any desired shape and size including round, oval, oblong cylindrical, or polygonal. In one such embodiment, the surfaces of the immediate release dosage form may be flat, round, concave, or convex.

In particular, when the immediate release formulations are prepared as a tablet, the immediate release tablets contain a relatively large percentage and absolute amount of the compound and so are expected to improve patient compliance and convenience, by replacing the need to ingest large amounts of liquids or liquid/solid suspensions. One or more immediate release tablets as described herein can be administered, by oral ingestion, e.g., closely spaced, in order to provide a therapeutically effective dose of the compound to the subject in a relatively short period of time.

Where desired or necessary, the outer surface of an immediate release dosage form may be coated, e.g., with a color coat or with a moisture barrier layer using materials and methods known in the art.

In some embodiments, one aspect of the invention relates to an immediate release compressed tablet for oral deliver, of the compound of Formula I, the tablet comprising:
  the compound of Formula I or a pharmaceutically acceptable salt thereof in an amount of about 90-98% by weight of the tablet;
  at least one hinder in an amount of about 1-5% by weight of the tablet; and
  at least one lubricant in an amount of about 0.1-2% by weight of the tablet;
  wherein the tablet releases at least 85% of the compound of Formula I or a pharmaceutically acceptable salt thereof contained therein within a period of less than 15 minutes after administration of the tablet to a subject.

In one embodiment, the tablet comprises:
  the compound of Formula I or a pharmaceutically acceptable salt thereof in an amount of about 91-95% by weight of the tablet;
  at least one hinder in an amount of about 2-3% by weight of the tablet;
  at least one lubricant in an amount of about 0.1-1% by weight of the tablet; and optionally, a cosmetic film coat in an amount of about 3-4% by weight of the tablet;
  wherein the tablet releases at least 85% of the compound of Formula I or a pharmaceutically acceptable salt thereof contained therein within a period of less than 15 minutes after administration of the tablet to a subject.

In one embodiment, the tablet comprises:
  the compound of Formula I or a pharmaceutically acceptable salt thereof in an amount of about 93.22% by weight of the tablet;
  at least one binder (e.g., hydroxypropylcellulose) in an amount of about 2.87% by weight of the tablet;
  at least one lubricant (e.g., magnesium stearate) an amount of about 0.52% by weight of the tablet; and
  optionally, a cosmetic film coat (e.g., Opadry® II yellow) in an amount of about 3-4% by weight of the tablet;
  wherein the tablet releases at least 85% of the compound of Formula I or a pharmaceutically acceptable salt thereof contained therein within a period of less than 15 minutes after administration of the tablet to a subject.

The invention further relates to an immediate release oral dosage form of the compound of Formula I, the oral dosage form comprising:

the compound of Formula I or a pharmaceutically acceptable salt thereof in an amount of about 90-98% by weight of the oral dosage form;
at least one binder in an amount of about 1-5% by weight of the oral dosage form; and
at least one lubricant in an amount of about 0.1-2% by weight of the oral dosage form;
wherein the oral dosage form releases at least 85% of the compound of Formula I or a pharmaceutically acceptable salt thereof contained therein within a period of less than 15 minutes after administration of the oral dosage form to a subject.

The formulations and unit dosage forms provided herein can be utilized to achieve immediate release of the compound of Formula I, as well as pharmaceutically acceptable salts, hydrates, isomers, including tautomers, solvates and complexes of the compound of Formula I.

In some embodiments, the tablet releases at least 85%, 86%, 87%, 88%, 89%, 90%, 91%, 92%, 93%, 94%, 95%, 96%, 97%, 98%, or 99% of the compound of Formula I or a pharmaceutically acceptable salt thereof contained therein within a period of less than 15 minutes after administration of the tablet to a subject, e.g., less than 15, 14, 13, 12, 11, 10, 9, 8, 7, 6, or 5 minutes. In some embodiments, the tablet releases at least 95%, 96%, 97%, 98%, or 99% of the compound of Formula I or a pharmaceutically acceptable salt thereof contained therein within a period of less than 30 minutes after administration of the tablet to a subject.

In certain embodiments, the tablet does not comprise a disintegrant. The term "disintegrant," as used herein, refers to an agent added to a tablet to promote the breakup of the tablet in an aqueous environment. The tablets of the present invention are advantageous in that they dissolve rather than disintegrate, In the present invention the presence of disintegrant in the formulation may actually slow down release of the compound of Formula I.

In certain embodiments, the compound of Formula I or a pharmaceutically acceptable salt thereof is present in an amount of about 90%, 90.5%, 91%, 91.5%, 92%, 92.5%, 93%, 93.5%, 94%, 94.5%, 95%, 95.5%, 96%, 96.5%, 97%, 97.5%, or 98% by weight of the tablet or any value or range therein. In certain embodiments, the compound of Formula I or a pharmaceutically acceptable salt thereof is present in an amount of about 90% to about 98%, about 92% to about 98%, about 94% to about 98%, about 96% to about 98%, about 90% to about 92%, about 90% to about 94%, about 90% to about 96%, about 92% to about 94%, about 92% to about 96%, or about 94% to about 96%.

In certain embodiments, the at least one binder is present in an amount of about 1%, 1.5%, 2%, 2.5%, 3%, 3.5%, 4%, 4.5%, or 5% by weight of the tablet or any value or range therein. In certain embodiments, the at least one binder is present in an amount of about 1% to about 5%, about 2% to about 5%, about 3% to about 5%, about 4% to about 5%, about 1% to about 2%, about 1% to about 3%, about 1% to about 4%, about 2% to about 3%, about 2% to about 4%, or about 3% to about 4%. The tablet may comprise at least one binder, e.g., 1, 2, 3, 4, 5, or more binders.

In certain embodiments, the at least one binder is selected from at least one of hydroxypropyl cellulose, ethylcellulose, hydroxypropyl methylcellulose, polyvinyl alcohol, hydroxy ethyl cellulose, povidone, copovidone, pregelatinized starch, dextrin, gelatin, maltodextrin, starch, zein, acacia, alginic acid, carbomers (cross-linked polyacrylates), polymethacrylates, sodium carboxymethylcellulose, guar gum, hydrogenated vegetable oil (type 1), methylcellulose, magnesium aluminum silicate, and sodium alginate or any combination thereof. In some embodiments, the at least one binder is hydroxypropyl cellulose.

In certain embodiments, the at least one lubricant is present in an amount of about 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, or 2.0% by weight of the tablet or any value or range therein. In certain embodiments, the at least one lubricant is present in an amount of about 0.1% to about 2.0%, about 0.5% to about 2.0%, about 1.0% to about 2.0%, about 1.5% to about 2.0%, about 0.1% to about 0.5%, about 0.1% to about 1.0%, about 0.1% to about 1.5%, about 0.5% to about 1.0%, about 0.5% to about 1.5%, or about 1.0% to about 1.5%. The tablet may comprise at least one lubricant, e.g., 1, 2, 3, 4, 5, or more lubricants. Where the immediate release formulation is provided as a tableted dosage form, still lower lubricant levels may be achieved with use of a "puffer" system during tableting. Such systems are known in the art, commercially available and apply lubricant directly to the punch and die surfaces rather than throughout the formulation.

In certain embodiments, the at least one lubricant is selected from at least one of magnesium stearate, stearic acid, calcium stearate, hydrogenated castor oil, hydrogenated vegetable oil, light mineral oil, magnesium stearate, mineral oil, polyethylene glycol, sodium benzoate, sodium stearyl fumarate, and zinc stearate or any combination thereof. In some embodiments, the at least one lubricant is magnesium stearate. In other embodiments, magnesium stearate may be used in combination with one or more other lubricants or a surfactant, such as sodium lauryl sulfate. In particular, if needed to overcome potential hydrophobic properties of magnesium stearate, sodium lauryl sulfate may also be included when using magnesium stearate (Remington: the Science and Practice of Pharmacy, $20^{th}$ edition, Gennaro, Ed., Lippincott & Wilkins (2000)).

In some embodiments, the at least one binder is hydroxypropyl cellulose. In some embodiments, the at least one lubricant is magnesium stearate. In some embodiments, the at least one binder is hydroxypropyl cellulose and the at least one lubricant is magnesium stearate.

In certain embodiments, the tablet is coated. The coating may be, without limitation, a color overcoat.

In some embodiments, the compound of Formula I or a pharmaceutically acceptable salt thereof is a hydrochloride salt of the compound.

The tablet may be any shape that is suitable for immediate release and allows the release of at least 85% of the compound of Formula I or a pharmaceutically acceptable salt thereof contained therein within a period of less than 15 minutes after administration of the tablet to a subject. In some embodiments, the tablet maximizes surface area to volume ratio to promote rapid dissolution. In some embodiments, the tablet is oblong in shape.

The tablet may contain any amount of the compound of Formula I or a pharmaceutically acceptable salt thereof suitable for administration as a unit dosage form. In some embodiments, the tablet contains about 1 mg to about 1000 mg of the drug or any range or value therein, e.g., about 10 mg to about 500 mg, e.g., about 37.5 mg, about 75 mg, about 150 mg, or about 300 mg.

Methods are disclosed herein to treat conditions amenable to treatment by APC, by administering an effective amount of one or more dosage forms as described herein. For example, the present dosage forms can be administered to treat a subject in need of treatment for narcolepsy, cataplexy, excessive daytime sleepiness, drug addiction, sexual dysfunction, fatigue, fibromyalgia, attention deficit/hyperactivity, disorder, restless legs syndrome, depression, bipolar disorder, or obesity, or to promoting smoking cessation in a subject in need thereof. See, e.g., U.S. Pat. Nos. 8,232,315; 8,440,715; 8,552,060; 8,623,913; 8,729,120; 8,741,950; 8,895,609; 8,927,602; 9,226,910; and 9,359,290; and U.S. Publication Nos. 2012/0004300 and 2015/0018414; each of which is incorporated by reference in its entirety with respect to the disorder to be treated.

Compounds of the invention that have similar affinity for the dopamine transporter (DAT) and alpha2 adrenergic receptors (see binding profile in Example 2) may be useful as pro-cognitive agents and as treatments for post-traumatic stress disorder (PTSD). Specifically, compounds such as methylphenidate (Ritalin, Concerta) that inhibit the reuptake of dopamine (DA) at the DAT have been shown to be efficacious in disorders of attention and cognition such as attention deficit hyperactivity disorder (AMID). Increases in DA signaling can increase creative thinking and attentional focus. In addition, inhibition of reuptake at the DAT can also inhibit reuptake of norepinephrine (NE) and increase NE signaling. NE has high affinity for alpha2 adrenergic receptors, and activity at alpha2 receptors has been shown to strengthen pre-frontal cortex (PFC) delay-related firing and improve PFC function. Thus, the compounds of the invention may be useful for treating disorders that involve impaired attention, attentional processing, cognition, or executive function including psychiatric conditions such as ADHD, bipolar depression, major depressive disorder, schizoaffective disorders, and PTSD; and in neurological conditions such as Alzheimer's Disease, Parkinson's Disease, all forms of dementia, and multiple sclerosis. One aspect of the invention therefore relates to a method of inducing a pro-cognitive effect in a subject in need thereof, comprising administering to the subject the a compound of the invention.

In addition to the pro-cognitive effects described above, compounds of the invention that have similar affinity for the dopamine transporter (DAT) and alpha2 adrenergic receptors may be useful for treating nightmares and sleep-related disturbances associated with PTSD. Prazocin is an alpha1 receptor antagonist that has been used to treat symptoms of PTSD. The compounds of the invention may be useful in treating symptoms of PTSD based on their similar activity at alpha adrenergic autoreceptors. Activity at alpha2 receptors can impair the emotional responding of the amygdala, which when coupled with the strengthening of firing in the PFC, could lead to reduced emotional responsivity and enhanced executive function in PTSD. Thus, another aspect of the invention relates to a method of treating nightmares and/or sleep-related disturbances associated with PTSD in a subject in need thereof, comprising administering to the subject the a compound of the invention.

The dosage forms disclosed herein can also be provided as a kit comprising, for example, separately packaged, a container comprising a plurality of immediate release tablets or capsules, which tablets or capsules can be individually packaged, as in foil envelopes or in a blister pack. The tablets or capsules can be packaged in many conformations with or without desiccants or other materials to prevent ingress of water. Instruction materials or means, such as printed labeling, can also be included for their administration, e.g., sequentially over a preselected time period and/or at preselected intervals, to yield the desired levels of the compound in vivo for preselected periods of time, to treat a preselected condition.

A daily dose of about 1 to about 2000 mg of the compound of the invention or a pharmaceutically acceptable salt thereof may be administered to accomplish the therapeutic results disclosed herein, For example, a daily dosage of about 10-1000 mg, e.g., about 20-500 mg, in single or divided doses, is administered. In some embodiments, the daily dose may be about 0.01 to about 150 mg/kg body weight, e.g., about 0.2 to about 18 mg/kg body weight.

In one embodiment of the invention, the compound of the invention is administered to the subject as needed to treat a disorder. The compound can be administered continuously or intermittently. In one embodiment, the compound is administered to the subject more than once a day, e.g., 2, 3, or 4 times per day, or once every 1, 2, 3, 4, 5, 6, or 7 days, In another embodiment, the compound is administered to the subject no more than once a week, e.g., no more than once every two weeks, once a month, once every two months, once every three months, once every four months, once every five months, once every six months, or longer. In a further embodiment, the compound is administered using two or more different schedules, e.g., more frequently initially (for example to build up to a certain level, e.g., once a day or more) and then less frequently (e.g., once a week or less). In other embodiments, the compound can be administered by any discontinuous administration regimen. In one example, the compound can be administered not more than once every three days, every four days, every five days, every six days, every seven days, every eight days, every nine days, or every ten days, or longer. The administration can continue for one, two, three, or four weeks or one, two, or three months, or longer. Optionally, after a period of rest, the compound can be administered under the same or a different schedule. The period of rest can be one, two, three, or four weeks, or longer, according to the pharmacodynamic effects of the compound on the subject. In another embodiment the compound can be administered to build up to a certain level, then maintained at a constant level and then a tailing dosage.

In one aspect of the invention, the compound of the invention is delivered to a subject concurrently with an additional therapeutic agent. The additional therapeutic agent can be delivered in the same composition as the compound or in a separate composition. The additional therapeutic agent can be delivered to the subject on a different schedule or by a different route as compared to the compound. The additional therapeutic agent can be any agent that provides a benefit to the subject. Further agents include, without limitation, stimulants, anti-psychotics, anti-depressants, agents for neurological disorders, and chemotherapeutic agents. One therapeutic agent that can be administered daring the same period is Xyrem®, sold commercially by Jazz Pharmaceuticals, which is used to treat narcolepsy and cataplexy. See U.S. Pat. Nos. 8,952,062 and 9,050,302.

The present invention finds use in research as well as veterinary and medical applications. Suitable subjects are generally mammalian subjects. The term "mammal" as used herein includes, but is not limited to, humans, non-human primates, cattle, sheep, goats, pigs, horses, cats, dog, rabbits, rodents (e.g., rats or mice), etc. Human subjects include neonates, infants, juveniles, adults and geriatric subjects.

In particular embodiments, the subject is a human subject that has a disorder amenable to treatment with APC. In other embodiments, the subject used in the methods of the invention is an animal model of a disorder amenable to treatment with APC.

The subject can be a subject "in need of" the methods of the present invention, e.g., in need of the therapeutic effects of the inventive methods. For example, the subject can be a subject that is experiencing a disorder amenable to treatment with APC, is suspected of having a disorder amenable to treatment with APC, and/or is anticipated to experience a disorder amenable to treatment with APC, and the methods and compositions of the invention are used for therapeutic and/or prophylactic treatment.

The present invention is explained in greater detail in the following non-limiting Examples.

EXAMPLE 1

Synthesis of Compound 2

APC (15.0 g) and sodium cyanate (6.4. g) were suspended in methylene chloride (150 mL) and cooled in an ice-bath. Methanesulfonic acid (10.6 mL) was added dropwise into the reaction mixture over a 45 min period. The ice-bath was removed, and the reaction mixture was stirred overnight at room temperature. The reaction was not complete and an extra amount of sodium cyanate (4.2. g) and methanesulfonic acid (4.2 mL) was added after the reaction mixture was cooled in an ice-bath. After stirring at room temperature for another 6 hours, the reaction mixture was cooled in an ice-bath, and the acidic pH of the reaction mixture was adjusted to a pH of about 9 by adding 10% aqueous sodium hydroxide. The organic phase was separated and washed with brine, then dried over anhydrous sodium sulfate, filtered, and concentrated to yield the desired product as a white solid (5.7 g). 1H NMR (DMSO-d6, δ ppm): 2.49-2.51 (1H, m), 2.62 (1H, dd, J=3.9, 5.9 Hz) 3.10 (1H, m), 3.32 (3H, s, hr), 3.82 (1H, dd, J=6.5, 5.4 Hz), 3.90 (1H, dd, 5.1 Hz), 7.06-7.32 (7H, m).

The free base obtained in the above procedure was dissolved in methanol (20 mL) and 4.5 N hydrogen chloride solution in isopropanol (5.8 mL) was added in to the mixture and the mixture was placed in a refrigerator. White precipitate was collected by filtration and washed with acetone followed by ethyl ether. After drying the product weight 5.9 g (90.2%). m.p. (uncorr.): 199.1-199.2° C. 1H NMR (DMSO-d6, δ ppm): 2.89 (1H, dd, J=12.9, 9.5 Hz), 3.10 (1H, dd, J=13.5, 5.2 Hz, 3.38 (1H, s, br), 3.98 (1H, dd, J=11.5, 6.0 Hz), 4.20 (1H, dd, J=11.7, 2.1 Hz), 7.14-7.37 (7H, m), 8.46 (3H, s, br), 9.76 (1H, s). Elemental analysis: Calculated C, 48.27%, H, 5.89%, N, 15.35%; Found C, 48.36%, H, 5.82%, N, 15.18%; C, 48.50%, H, 5.86%, N, 15.39%.

EXAMPLE 2

Characterization of Binding Profile

Compound 2 was tested for pharmacological activity in comparison to APC. Eight binding assays were carried out to provide a binding profile for each compound, including binding to dopamine transporter (DAT), norepinephrine transporter (NET), serotonin (5-HT) transporter (SERT), alpha2A adrenergic receptor (Alpha2A), alpha2C adrenergic receptor (Alpha2C), D2S dopamine receptor (D2S), D2L, dopamine receptor (D2L), and vesicular monoamine transporter (VMAT2). Competitive binding assays using a radiolabeled ligand were carried out with each compound at 10 μM. The radioligand for each target was as follows: DAT—BTCP, NET—protriptyline, SERT—imipramine Alpha2A—yohimbine, Alpha2C—yohimbine, D2S—7-OH-DPAT, D2L—butaclamol, VMAT2—tetrabenazine. The source of the receptors and transporters were prepared cell membrane fractions.

Results are shown in Table 1. The similarity in binding profiles of APC and compound 2 is indicative of similar biological activity.

TABLE 1

| | Binding profile | | | | | | | |
| --- | --- | --- | --- | --- | --- | --- | --- | --- |
| | % Inhibition of Binding at Each Transporter or Receptor Target | | | | | | | |
| Compound | Alpha2A | Alpha2C | D2S | D2L | NET | DAT | SERT | VMAT2 |
| APC | 16.5 | 7.4 | 18.7 | −3.4 | 6.2 | 81.4 | 4.0 | 12.0 |
| Compound 2 | 28.0 | 52.1 | 11.8 | −5.5 | 2.7 | 80.6 | 3.4 | −1.0 |

The foregoing is illustrative of the present invention, and is not to be construed as limiting thereof. The invention is defined by the following claims, with equivalents of the claims to be included therein. All publications, patent applications, patents, patent publications, and any other references cited herein are incorporated by reference in their entireties for the teachings relevant to the sentence and/or paragraph in which the reference is presented.

What is claimed is:

1. A method of treating narcolepsy, cataplexy, excessive daytime sleepiness, drug addiction, sexual dysfunction, fatigue, fibromyalgia, restless legs syndrome, depression, bipolar disorder, or obesity in a subject in need thereof, or promoting smoking cessation in a subject in need thereof, comprising administering to the subject compound 1:

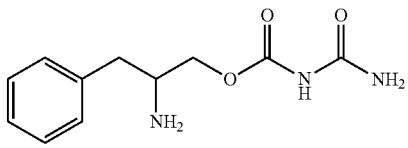

or a pharmaceutically acceptable salt thereof.

2. A method of inducing a pro-cognitive effect in a subject in need thereof, comprising administering to the subject compound 1:

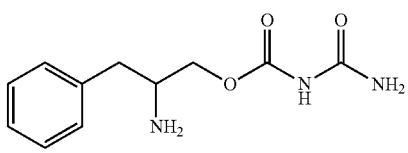

or a pharmaceutically acceptable salt thereof;

wherein the subject has bipolar depression, major depressive disorder, PTSD, or Parkinson's Disease.

3. A method of treating nightmares and/or sleep-related disturbances associated with PTSD in a subject in need thereof, comprising administering to the subject compound 1:

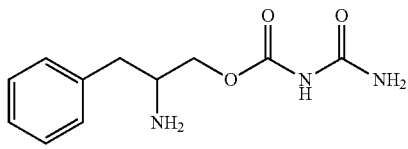

or a pharmaceutically acceptable salt thereof.

4. The method of claim 1, wherein the compound is compound 2:

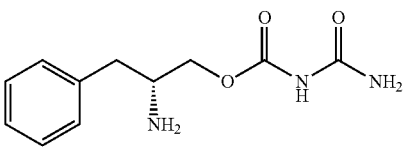

or a pharmaceutically acceptable salt thereof.

5. The method of claim 1, comprising administering a pharmaceutical composition comprising the compound and a pharmaceutically acceptable carrier.

6. The method of claim 5, wherein the composition is a dosage form.

7. The method of claim 6, wherein the composition is an immediate release oral dosage form.

8. The method of claim 7, wherein the composition is a tablet or a capsule.

9. The method of claim 2, wherein the compound is compound 2:

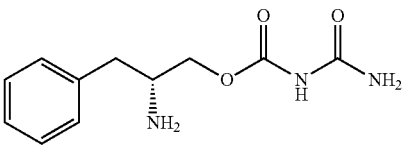 [SMILES: NC(=O)NC(=O)OCC(N)Cc1ccccc1]

or a pharmaceutically acceptable salt thereof.

10. The method of claim 2, comprising administering a pharmaceutical composition comprising the compound and a pharmaceutically acceptable carrier.

11. The method of claim 10, wherein the composition is a dosage form.

12. The method of claim 11, wherein the composition is an immediate release oral dosage form.

13. The method of claim 12, wherein the composition is a tablet or a capsule.

14. The method of claim 3, wherein the compound is compound 2:

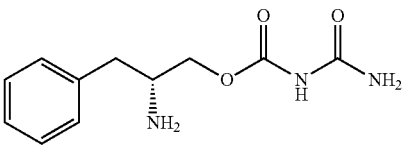 [SMILES: NC(=O)NC(=O)OCC(N)Cc1ccccc1]

or a pharmaceutically acceptable salt thereof.

15. The method of claim 3, comprising administering a pharmaceutical composition comprising the compound and a pharmaceutically acceptable carrier.

16. The method of claim 15, wherein the composition is a dosage form.

17. The method of claim 16, wherein the composition is an immediate release oral dosage form.

18. The method of claim 17, wherein the composition is a tablet or a capsule.

* * * * *

UNITED STATES PATENT AND TRADEMARK OFFICE
CERTIFICATE OF CORRECTION

PATENT NO. : 11,780,805 B2
APPLICATION NO. : 17/470063
DATED : October 10, 2023
INVENTOR(S) : Hurley et al.

It is certified that error appears in the above-identified patent and that said Letters Patent is hereby corrected as shown below:

In the Specification

Column 8, Line 29: Please correct "hinder" to read --binder--

Column 8, Line 41: Please correct "hinder" to read --binder--

Column 13, Line 45: Please correct "(3H, s, hr)" to read --(3H, s, br)--

Column 13, Lines 45-46: Please correct "(1H, dd, 5.1 Hz)" to read --(1H, dd, J=10.5, 5.1 Hz)--

Column 13, Lines 57-59: Please correct "Calculated C, 48.27%, H, 5.89%, N, 15.35%; Found C, 48.36%, H, 5.82%, N, 15.18%; C, 48.50%, H, 5.86%, N, 15.39%." to read --Calculated C 48.27%, H 5.89%, N 15.35%; Found C 48.36%, H 5.82%, N 15.18%; C 48.50%, H 5.86%, N 15.39%.--

Signed and Sealed this
Thirteenth Day of February, 2024

Katherine Kelly Vidal
*Director of the United States Patent and Trademark Office*